United States Patent [19]

Boone et al.

[11] Patent Number: 5,059,410

[45] Date of Patent: Oct. 22, 1991

[54] PRODUCTION OF SILICON

[75] Inventors: James E. Boone; David W. Owens; Robert E. Farritor, all of Baton Rouge, La.; Wesley D. Blank, Pasadena, Tex.

[73] Assignee: Ethyl Corporation, Richmond, Va.

[21] Appl. No.: 221,657

[22] Filed: Jul. 20, 1988

Related U.S. Application Data

[60] Continuation of Ser. No. 59,565, Jun. 8, 1987, abandoned, which is a division of Ser. No. 761,434, Aug. 1, 1985, abandoned.

[51] Int. Cl.⁵ .......................................... C01B 33/027
[52] U.S. Cl. ..................................... 423/349; 118/716; 422/139; 427/213
[58] Field of Search ................ 423/348, 349; 427/213; 118/716; 422/139; 222/487, 152

[56] References Cited

U.S. PATENT DOCUMENTS

| | | | |
|---|---|---|---|
| 4,098,224 | 7/1978 | Noren et al. | 118/49 |
| 4,154,870 | 5/1979 | Wakefield | 427/8 |
| 4,381,898 | 5/1983 | Rotolico et al. | 406/137 |
| 4,391,860 | 7/1983 | Rotolico et al. | 118/308 |
| 4,424,199 | 1/1984 | Iya | 423/349 |
| 4,684,513 | 8/1987 | Iya | 423/349 |
| 4,691,866 | 9/1987 | Belk | 241/10 |

Primary Examiner—Olik Chaudhuri
Attorney, Agent, or Firm—P. M. Pippenger

[57] ABSTRACT

An apparatus and process for maintaining the purity of solid/granular product and dispensing high purity granular product from a vessel. A noncontaminating surface is provided by a cup, cylinder, or other structure having a surface of silicon, silicon carbide, silicon nitride, sialon, or similar materials and preferably operates as an angle of repose valve in a pressurized system to prevent contamination by undue contact of the high purity product with conventional gastight valves such as ball valves, butterfly valves, pinch valves, etc.

6 Claims, 4 Drawing Sheets

PRODUCTION OF SILICON

CROSS REFERENCE TO RELATED APPLICATION

This application is a continuation of application Ser. No. 59,565, filed June 8, 1987, which in turn is a division of application Ser. No. 761,434, filed Aug. 1, 1985 both now abandoned.

BACKGROUND OF THE INVENTION

This invention relates in general to maintaining the purity of a high purity material in a pressurized system and dispensing such material. This invention relates in particular to processes, apparatuses, and valves for dispensing a high purity material from a pressurized vessel by depositing the high purity material on a noncontaminating surface and then transferring it only when a gastight valve is opened to dispense the solid material.

Various types of standard valves have been used in the past to dispense gaseous, solid, and liquid materials. However, applicants have found that standard valves are unacceptable for dispensing relatively hard solids that may cause valve wear. In preserving the high purity of a granular or similar solid product, valve wear also has the disadvantage of contaminating the solid product with the metal, elastomers, or other material from which the valve is constructed. That is, not only do the valves wear out prematurely and lose their gas seal but for high purity applications, the material that wears the valves becomes contaminated with impurities from the valve body. For example, a mechanically operated or gas operated elastomeric pinch valve has been used to shut the opening of the valve, trapping between the elastomatic walls of the valve particles of granular or similar solid product but making a gastight seal. The continued opening and closing of the elastomatic valve continues to wear on the walls of the valve so as to make the valve lose its gas seal. Similarly, ball valves and butterfly valves wear and lose their gas seal. In the process of losing the gas seal, such valves concurrently contaminate a high purity granular or similar material with carbon, phosphorus, boron, nickel, or other elements present in the valve walls. Metals are particularly troublesome, especially for dispensing semiconductor materials.

When a high purity granular material such as silicon granules, gallium arsenide particles, or other III-V semiconductor materials, for example, are contained in a pressurized vessel, they will necessarily become somewhat contaminated by use of only a standard, gastight valve as described above. While this contamination may seem very minor to the casual observer, the contamination is very significant when the purity of the granules or similar material is to be maintained in the parts per million, parts per billion, or even parts per trillion range.

In certain pressurized vessels, the granules or other forms of solid are at relatively high temperature which can accelerate the process of wearing out the valve and increase the rate of contamination of the high purity material from the walls or other surfaces of the valve.

SUMMARY OF THE INVENTION

The present invention addresses the problems of valve wear and contamination of high purity solid products dispensed from a vessel by providing means for dispensing the high purity product in granular or similar form in such a fashion that the product does not have undue contact with the working mechanism of the gastight valve of the vessel. Normally the solids are being dispensed from a protective environment.

The invention may use an angle of repose valve and an accompanying gastight valve in a protective environment, preferably a gastight or pressurized environment. The protective environment may be a high purity zone and the pressurized environment may be one with a flow of gas.

An exemplary protective environment may be merely a zone for containing solids product apart from the atmosphere. In containing semiconductor solids, separation from the atmosphere prevents accumulation of carbon and other impurities otherwise gathered from dust and organic matter in the air. Thus, the protective environment may be a blanket of helium, argon, etc. Examples of such environments are pure atmosphere containers for dispensing high purity silicon seeds to a fluid bed reactor and the fluid bed reactor itself (a pressurized environment).

By use of the combination of the invention it is possible to stop the flow of a solids material in the protective environment in such a manner that the high purity solid is not contacted with the gastight valve during its operation. There is then substantially no contact between the high purity solid and the gastight valve during discharge of the solids from the dispensing means through the gastight valve to a collection vessel, hopper, or other container. The dispensing means preferably has noncontaminating surfaces for contacting the solids. The dispensing means is also preferably an angle of repose valve.

The dispensing means and angle of repose valves of the invention are preferably constructed of noncontaminating materials such that the contact of solids with the surface supporting the solids does not contaminate the solids.

Of course, even if noncontaminating materials are not used, valve wear is avoided by use of such a dispensing means. The angle of repose valve stops the flow of solids from a vessel when in a closed position and allows the solids to "seal" by virtue of their natural angle of repose against the valve seat. After solids flow has been interrupted, a gas sealing valve may now be closed to achieve the gastight seal. Product contamination is avoided because high purity solids flow is stopped in such a manner that the surfaces touching the high purity solid are of noncontaminating materials thus avoiding contamination. After the flow of solids has been stopped with the angle of repose valve, only then is the gastight valve allowed to close in a substantially solids-free environment, thus avoiding wear between the solid and the gastight valve and, desirably, avoiding contamination of the high purity solid.

BRIEF DESCRIPTION OF THE DRAWINGS

A better understanding of the present invention will be had upon reference to the following detailed description when read in conjunction with the accompanying drawings, in which.

DESCRIPTION OF THE PREFERRED EMBODIMENTS

Figure 1:
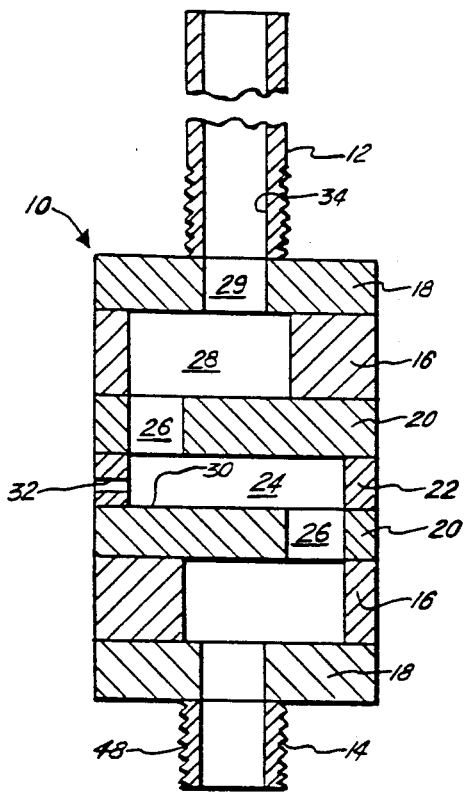
FIG. 1 is a cross-sectional view of an assembly of seven plates connected to an inlet and an outlet for solids.

According to the invention solids are dispensed from a vessel without wear to a gastight valve from contact between the gastight valve and the solids, especially without such contact during opening or closing of the gastight valve.

According to the invention a high purity solid, subject to a protective environment, is suitably dispensed from that environment without contaminating the high purity solid by the use of a noncontaminating means (such as an angle of repose valve) in combination with a gastight valve.

A preferred embodiment of the present invention is an apparatus for maintaining the purity of a solids product and dispensing said product from a vessel, said apparatus comprising:

(a) solids blocking means fluidly communicating with said vessel, said blocking means being operable between a first position to block the flow of and collect said product and a second position to discharge said product; and (b) valve means fluidly communicating with said blocking means to receive product discharged from said blocking means, said valve means being movable between a gastight closed position and an open position to receive the discharge from said blocking means and dispense said product from said vessel.

A preferred embodiment of the invention is also a process for dispensing a high purity solids product from a collection vessel having a gastight dispensing valve without eroding said dispensing valve, said process comprising the steps of:

(a) blocking the flow of said product from said vessel with a nongastight noncontaminating surface upstream of said gastight dispensing valve;

(b) opening said gastight dispensing valve; and (c) unblocking the flow of said product thereby discharging at least part of the collected product through said dispensing valve.

A preferred embodiment of the invention is also a process for the production of high purity silicon, said process comprising the steps of:

(a) fluidizing a heated bed of high purity silicon seed particles with a gas stream comprising a silicon-containing compound in a reactor having a gastight silicon product dispensing valve so as to decompose silicon-containing compound and coat said silicon seed particles to form high purity silicon product;

(b) blocking the flow of and collecting said high purity silicon product with noncontaminating surface below said heated bed and upstream of said gastight dispensing valve;

(c) opening said dispensing valve; and (d) unblocking the flow of and discharging said high purity silicon product [from said noncontaminating surface] through said open dispensing valve.

The apparatus of the present invention can take various physical forms and shapes so long as a noncontaminating means for stopping the flow of high purity solids is used in combination with a gastight valve means. The noncontaminating means may take various forms and shapes and suitable preferred embodiments of those structures for the noncontaminating means, especially angle of repose valves, and the surfaces for such noncontaminating means are given by way of example herein as well as in the accompanying drawings.

A preferred embodiment of the invention is also a high purity silicon fluid bed reactor comprising:

a fluidized bed reactor having walls defining a reaction chamber;

means for heating said reaction chamber to decompose a silicon-containing gas entering said chamber;

seed particle entry means for introducing silicon seed particles into said reaction chamber;

means for introducing a silicon-containing gas into said reaction chamber to decompose said gas and form silicon product by growing silicon on said silicon seed particles;

means for exhausting decomposition gas and any unreacted silicon-containing gas from said reaction chamber; and means for dispensing silicon product from said reactor, said dispensing means fluidly communicating with said reaction chamber and comprising:

noncontaminating solids blocking means for collecting and transferring said silicon product from said reaction chamber, and gastight valve means communicating with said blocking means to receive granular product discharged from said reaction chamber, and thereby dispense said silicon product from said reactor.

A preferred embodiment of the invention is also a device for maintaining the purity of a high purity solid product during transfer of said solid product from a high purity zone, said device comprising:

solids blocking means for collecting said product, said blocking means having surfaces for contacting said product, said surfaces being formed of a material noncontaminating to said product, said blocking means being operable to discharge said product therefrom; and valve means for discharging said product from said collection means, said valve means being operable between a gastight closed position and an open position to receive therethrough the discharge from said blocking means and thereby dispense said product.

A preferred embodiment of the invention is also an angle of repose valve for dispensing high purity solids from a protective environment, said valve comprising:

a housing having a top inlet and a bottom outlet;

an inlet tube sealingly disposed in said top inlet for receiving a flow of high purity solids from said protective environment, said inlet tube having a noncontaminating interior for contacting said solids;

high purity solids blocking means for controlling said flow of high purity solids, said blocking means being disposed within said housing and blocking but not contacting said inlet tube, said blocking means having noncontaminating surfaces for contacting said solids, said blocking means being movable within said housing between a first position to receive and block said high purity solids and accumulate solids in said inlet tube and a second position to unblock and discharge said high purity solids to said bottom outlet; and means for moving said blocking means between said first position and said second position, said moving means being controllable from outside said housing.

In one preferred embodiment, the invention is an apparatus for maintaining the purity of a granular solid product during discharge from a storage vessel, said apparatus including:

(a) a vessel adapted to store granular solid product;

(b) a receiving vessel below said adapted vessel to receive said granular solid product;

(c) passage means forming a fluid connection between said vessel and said receiving vessel;

(d) noncontaminating nongastight solids blocking means in said passage means; and (e) gastight valve means in said passage means between said nongastight solids blocking means and said storage vessel whereby said gastight valve means can be opened and closed without errosion caused by the passage of said granular solid product through said gastight valve means during opening and closing thereby prolonging the gastight life of said gastight valve and avoiding contamination of said solid product.

The solid products (solids) of the invention include all solids which are comprised of a large number of particles, granules, hunks, lumps, bits, fragments, shreddings, slivers, pieces, chunks, BB's, and other moieties to make up a bulk.

According to the invention, a vessel may be considered to include a gastight valve and a solids-tight valve for dispensing product in a noncontaminating manner.

Figure 11:
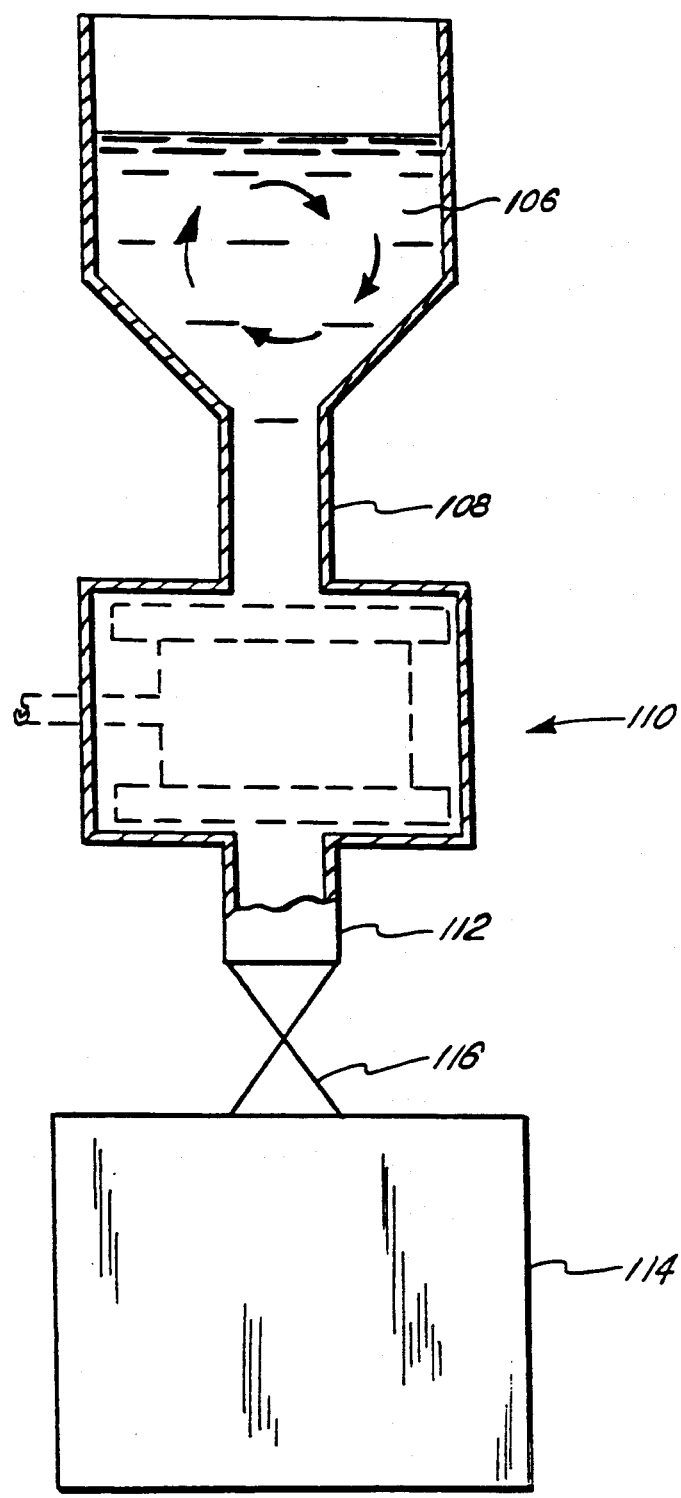
FIG. 11 is a schematic of a fluid bed, solids blocking means, and hopper for solids handling.

The invention may be generally described by reference to FIG. 11. A container vessel 106 such as a seed particle bin, fluidized bed reactor or storage tank contains high purity solid product. The vessel 106 fluidly communicates through conduit 108 to a means 110 for alternately blocking and permitting the flow of high purity solids. The high purity solids may be transferred from the blocking means 110 through second fluid communication means 112 for bulk collection in a hopper 114 or other device by transfer through a gastight valve 116. Preferably, the gastight valve 116 is positioned and constructed such that high purity product passes through it without touching valve 116. Operation of the above-described apparatus permits preservation of the high purity solid in a controlled environment without contacting a gastight valve which could contaminate the solid and erode the valve.

Figure 2:
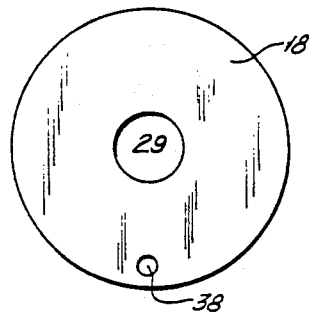
FIG. 2 is a top view of one of the end plates of the assembly.
Figure 3:
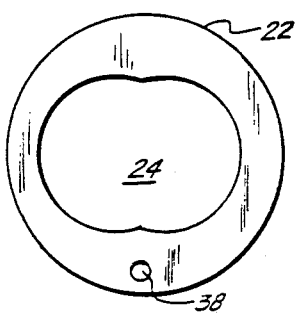
FIG. 3 is a top view of the center plate of the assembly.
Figure 4:
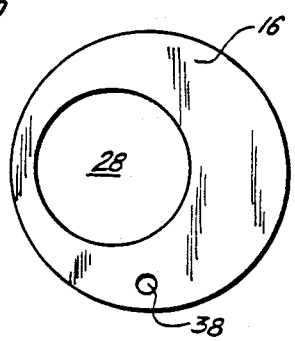
FIG. 4 is a top view of one of the next-to-end plates of the assembly.
Figure 5:
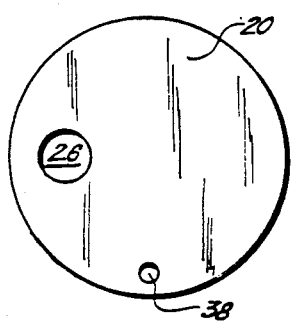
FIG. 5 is a top view of one of the next-to-center plates of the assembly.

In a preferred embodiment of the invention a noncontaminating means or means for avoiding valve wear is provided by a series of plates assembled as shown in FIG. 1 to form a gas operated angle of repose valve 10 which may be threadably or otherwise connected to a noncontaminating (silicon carbide-coated graphite or silicon) tube 12 from which it receives solids such as a granular product. An end plate 18 of this assembly is shown in FIG. 2. Another end plate 18 also threadably or otherwise connects to a dispensing tube 14. Two next-to-end plates 16, (FIG. 4) are oriented in the opposite directions and placed adjacent the end plates 18 in the assembly 10. Two next-to-center plates 20 shown in FIG. 5 are oriented opposite each other and placed adjacent each of the second plates 16 in the assembly 10 such that the openings between the adjacent plates 16 and 20 are aligned. Finally, the center plate 22 is placed between the third plates 20 to form the serpentine flow path shown in FIG. 1. Granular product or similar solids entering tube 12 from above will accumulate somewhat in the space 24 of center plate 22 and build up in the space 26 of the top next-to-center plate 20 as well as in space 28 of the top next-to-end plate 16, the space 29 of end plate 18, and the inside of tube 12.

Thus the assembly 10 provides an angle of repose valve which operates by simply providing a horizontal blocking surface below tube 12 carrying solids downward. The horizontal blocking surface, in this case surface 30 of bottom next-to-center plate 20 is wide enough that solids falling from above form a pile on it with a sloping surface angle equal to the angle of repose of the solids. That is, without motive force, the solids falling on surface 30 do not tend to fall down into opening 26 of bottom third plate 20 but rather tend to accumulate as described. Since the solids cannot flow out tube 14 they are blocked and accumulate up into tube 12 and above until a motive force is applied to transfer the solids from surface 30 thereby unblocking the solids flow.

In the assembly 10 shown in FIG. 1, the motive force may be applied by movement of the entire assembly, or other means such as the motion of a noncontaminating gas provided into gas inlet 32. The entire assembly 10 of FIG. 1 may be made of any noncontaminating material suitable for handling the pure product entering tube 12. Preferably, the inside diameter surface 34 of tube 12 and the remaining interior surfaces of the assembly which see the pure product, either while flow is stopped or during flow, are formed of the same material as the pure product or a composition including that material.

An angle of repose valve is particularly advantageous for the invention since a relatively small device may be used to accumulate solids product when used in conjunction with a tube or other container above the valve mechanism.

In a preferred embodiment of the invention, the high purity product is granular or BB-shaped silicon entering tube 12 and reposing on surface 30 and thereabove until moved such as by entry of argon, helium, or other gas through inlet 32. The angle of repose valve thus blocks the flow of solids and fluid bed from the fluidized bed reactor above the angle of repose valve. In such embodiment, the interior surfaces 34 and other interior surfaces of the assembly are preferably made of silicon, silicon carbide, silicon nitride, sialon (materials where the structural units are $(SiAl)(O,N)_4$ or $(Si,M)(O,N)_4$ tetrahedra where M is a metal), or another composition/alloy of silicon. Alternatively, the interior could be formed or coated with a noncontaminating glass, quartz, or silicon carbide-coated graphite. Alternatively, the entire assembly may be made of silicon carbide-coated graphite, silicon carbide, silicon nitride, or preferably, high purity silicon. In still another embodiment the surfaces which could contact silicon are coated by plasma-sprayed silicon on the steel or other metal.

Figure 7:
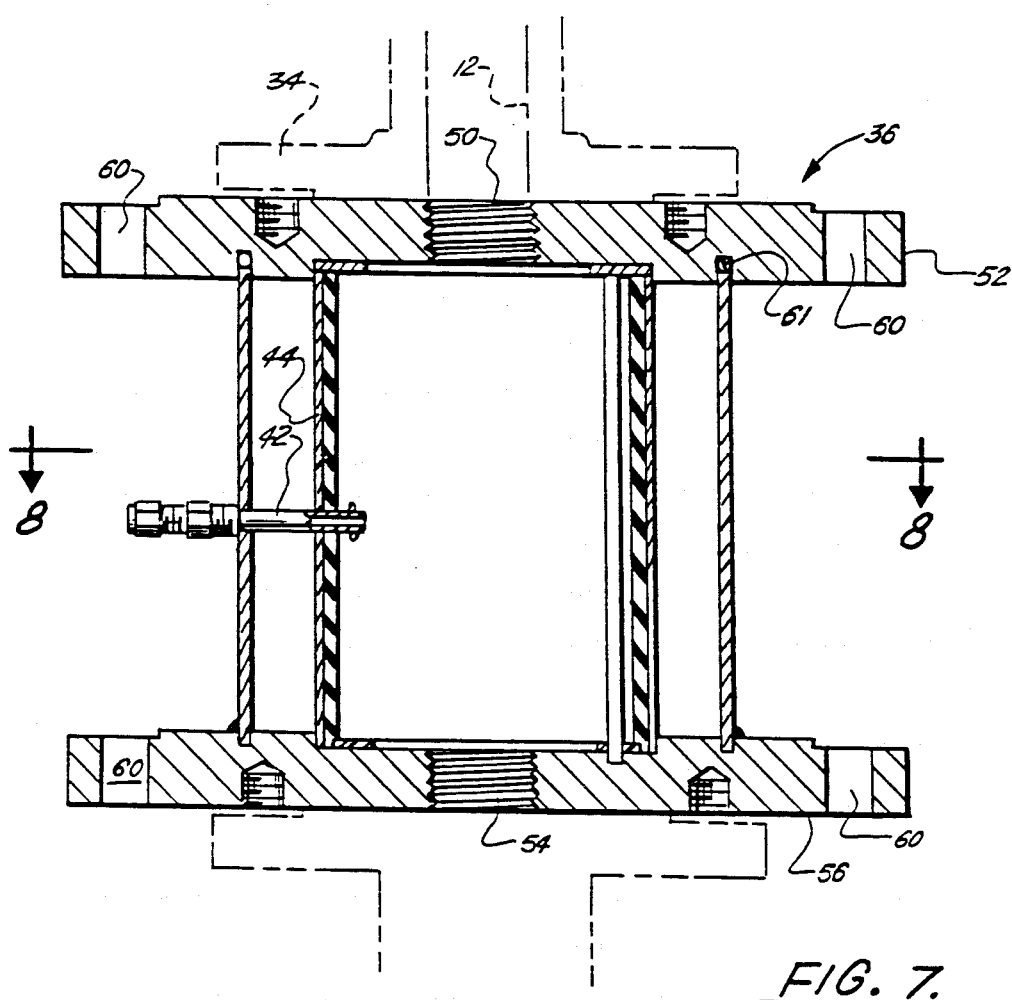
FIG. 7 is a center sectional view through FIG. 8.
Figure 8:
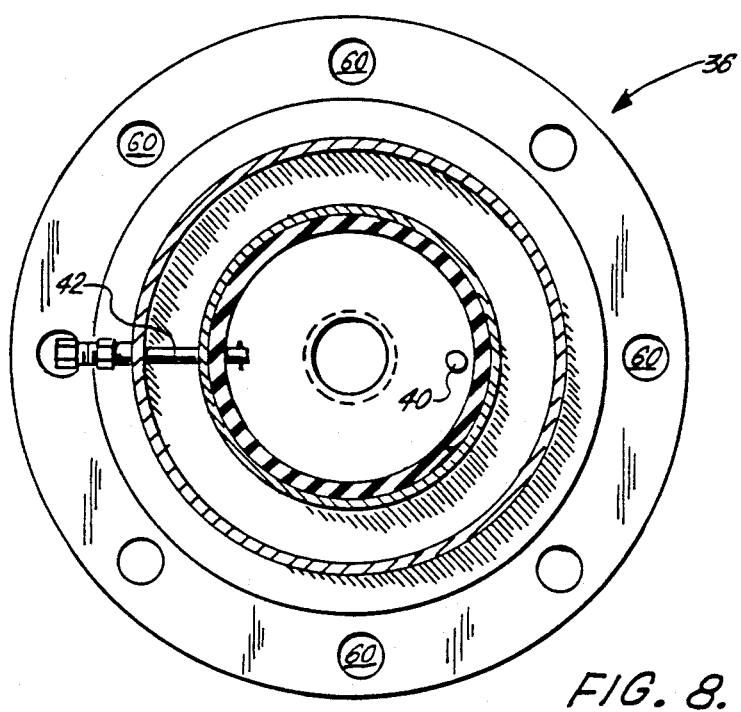
FIG. 8 is a cross-sectional end view of a gas operated noncontaminating means which may be operated as an angle of repose valve.

The entire assembly 10 of FIG. 1 is suitably disposed within an apparatus 36 shown in cross section in FIGS. 7 and 8. Each member plate, 18, 16, 20, 22, 20, 16, and 18 has a dowel hole 38 (two dowel holes and dowels may be used). The plates are assembled so that each of the dowel holes 38 are in line and the entire assembly may then be fitted into the apparatus 36 such that screw rod 40 received in the dowel holes 38 to maintain the rigid integrity of the assembly 10. A controlled supply of motive gas is connected to inlet tube 42 which is inserted through the interior wall 44 of apparatus 36 such that the inlet tube 42 projects into inlet 32 of the assembly 10.

In the above-described fashion, the noncontaminating internal assembly 10 may be positioned within an apparatus 36 made of any suitable material such as steel, stainless steel, or another metal. The exterior threaded wall 46 of tube 12 (FIG. 1) and threaded wall 48 of tube 14 are threadably received within the threaded openings 50 of plate 52 (FIG. 7) and threaded opening 54 of plate 56 in the apparatus 36 of FIG. 7.

A sectional top view of the apparatus 36, taken at the level of the inlet tube 42 but showing plate 52 is shown in FIG. 8. As can be seen, the entire apparatus 36 may be secured to the remainder of the flow path for the solid products by means of bolts or screws secured into threaded holes 58. Additionally, bolts may be attached through a series of holes 60 at the ends of plates 52 and 56 to secure the apparatus 36 tightly and make a gastight o-ring seal at 61.

Figures 6, 6A:
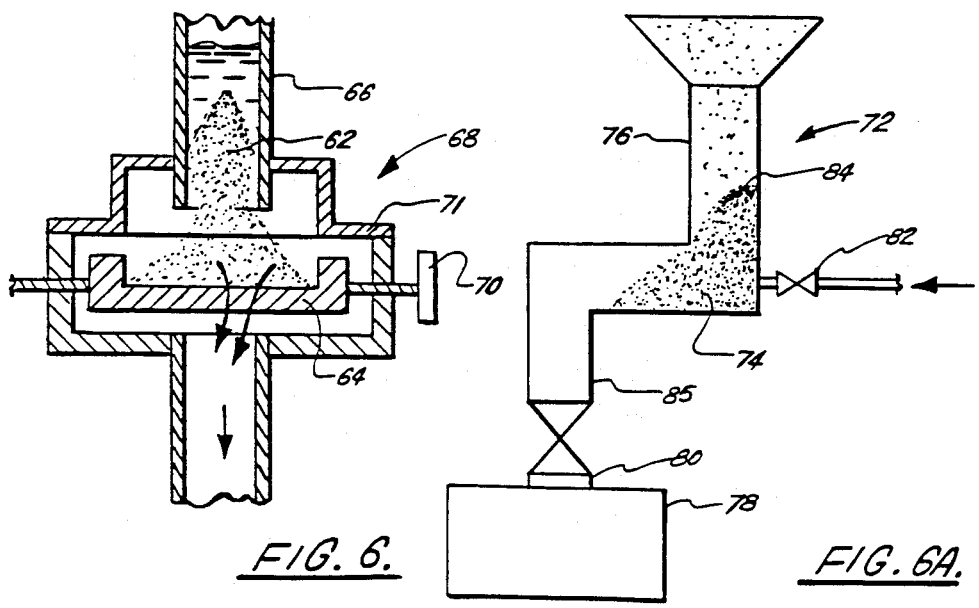
FIG. 6 is a schematic view of a cup-like angle of repose valve according to the invention.
FIG. 6A is a schematic of an elbow tube embodiment of an angle of repose valve.

Two alternative embodiments of the invention are shown in FIGS. 6 and 6A. FIG. 6 shows a flapper style angle of repose valve in the closed position with solid product 62 accumulated in the metal valve seat support 64 and accumulated in and above tube 66. The interior surfaces of tube 66 and metal valve seat support 64 which contacts solid product 62 are coated with a noncontaminating material according to the nature of the solid product 62.

In the case of granular silicon product, e.g., the interior surfaces of tube 66 and support 64 are formed of silicon carbide-coated graphite, silicon carbide, silicon nitride, sialon, silicon, or other noncontaminating material, preferably high purity silicon. The angle of repose valve 68 is operated so as to allow a buildup of solid product on a surface of support 64 and in tube 66 or a vessel above the valve. When the valve 68 is opened, solid product flows by gravity from above the valve. The product is collected not only immediately above the valve but in any tube or vessel above the valve before dispensing the product to a hopper or other container through a gastight valve (not shown) which may or may not be coated with or formed from noncontaminating materials. When valve 68 is used below a fluidized bed of solid product, the bed acts as a fluid such that if valve 68 remains open after accumulated solids are dispensed, then fluidized particles from the bed also begin to flow through valve 68. After the solid product 62 is collected in and above the valve 68, a gastight valve below the angle of repose valve 68 is opened and the collected solid product 62 is discharged from the valve seat support 64 by mechanically rotating handle 70 to discharge the collected silicon product 62 from the noncontaminating surfaces where the product 62 rests and above that position through the now opened gastight dispensing valve for collection, hoppering, packaging, or further processing.

If the angle of repose valve 68 shown in FIG. 6 or other apparatus of the invention is operated in a pressurized environment which contains a dangerous gas, it is advisable to discharge the silicon product from the angle of repose valve through the open gastight valve and into a hopper or similar container which is sealed from the outside and pressure equilized with the pressurized environment. For example, if the solid product is granular silicon formed from silane or a silane composition, this procedure will prevent the pyrophoric silane gas from escaping to the atmosphere. After the gastight valve below the angle of repose valve is again closed, the hopper apparatus may be purged or otherwise made safe by appropriate techniques. The entire valve 68 may be contained within a housing 71 which may be constructed of any suitable material.

A schematic view of another angle of repose valve 72 is shown in FIG. 6A. The solid product tends to accumulate at its natural angle of repose on surface 74 and build up in and above collection tube 76 as shown. The angle of repose valve 72 of FIG. 6A may be operated in much the same fashion as the angle of repose valve 68 shown in FIG. 6 except that a motive gas is used to move the solid product 84 from the surface 74 and from within collection tube 76 into a hopper 78. This is accomplished by opening gastight valve 80 and discharging a preferably noncontaminating motive gas through inlet valve 82 to move the solid product 84 through the lower portion of tube 76, through the open gastight valve 80 and into hopper 78. That is, the dispensed product may free fall in a contacting or, preferably, noncontacting manner to a collection hopper. In one preferred embodiment, the opening of the gastight valve is larger than and surrounds the tube through which solids flow. Of course it is always possible that some contact will occur between the open gastight valve and the solid product but this can be minimized by making the open I.D. of the gastight valve much larger than the drop tube 85. The resulting small amount of contact does not significantly contribute to contamination or valve wear. The invention is also advantageous because the solids do not contact the gastight valve during its operation.

After the desired amount of solid product 84 has been transferred to hopper 78, inlet valve 82 is closed causing solid product 84 to again accumulate on surface 74 to close the angle of repose valve. When gastight valve 80 clears of solids it is then closed.

Figure 9:
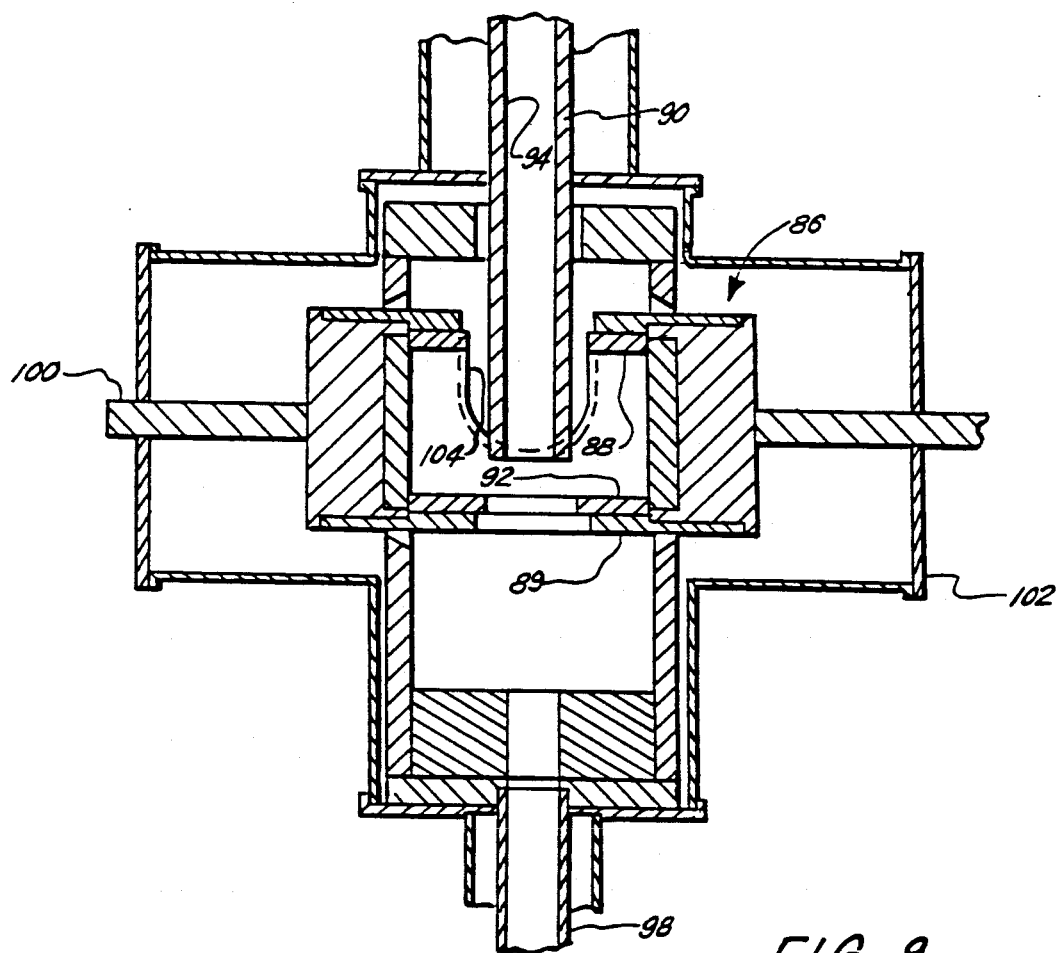
FIG. 9 is a cross-sectional view of a movable cylindrical noncontaminating means which rotates on its axis and may be operated as an angle of repose valve.

The angle of repose valve 86 shown open or unblocked in FIG. 9 permits collection of silicon product in a cylinder 88 in such a fashion that solid product collects in cylinder 88 and builds up inside and above collection and entry tube 90 thereby closing valve 86. Preferably, the inside surfaces 92 of cylinder 88 and 94 of tube 90 are coated with or formed of a material which is noncontaminating to the entering high purity solid product. Cylinder 88 has formed in its wall a hole 96 which, when the cylinder 88 is in the position shown in FIG. 9, permits solid product to flow from the cylinder 88 and, in fact, directly from tube 90 through hole 96 into dispensing tube 98 and through an open gastight valve (not shown) for collection of product.

Preferably, all of the inside surfaces of the angle of repose valve 86 shown in FIG. 9 which surfaces come into contact with the high purity solid product are coated with or formed of a material noncontaminating to the solid product. To close valve 86 rod 100 is rotated to move the cylinder 88 from the open position shown in FIG. 9 to a closed position wherein the hole 96 is above the bottom inside horizontal surface of cylinder 88 such that the solids falling from the tube 90 above form a pile on the cylinder inside wall with a sloping surface angle equal to the angle of repose of the solids.

Of course, eventually the solids build up into the tube 90 in a manner according to the shape, size, and particle size distribution of the solid product thereby preventing the solid product from flowing out hole 96 above the pile of solids. Thus the solids become blocked and begin to collect in tube 90 until the angle of repose valve 86 is opened by turning rod 100 to discharge the collected high purity product from the cylinder 88 through hole 96 into tube 98 and, preferably, through an open gastight valve for collection.

Suitably, a casing 102, which may be made of any substance such as stainless steel, carbon steel, or other material encloses the angle of repose valve 86 to maintain a high purity zone or environment. The high purity zone or environment may be associated with a gastight or even a pressurized zone open to the solids in the angle of repose valve 86 since the valve is not gastight.

Figure 10:
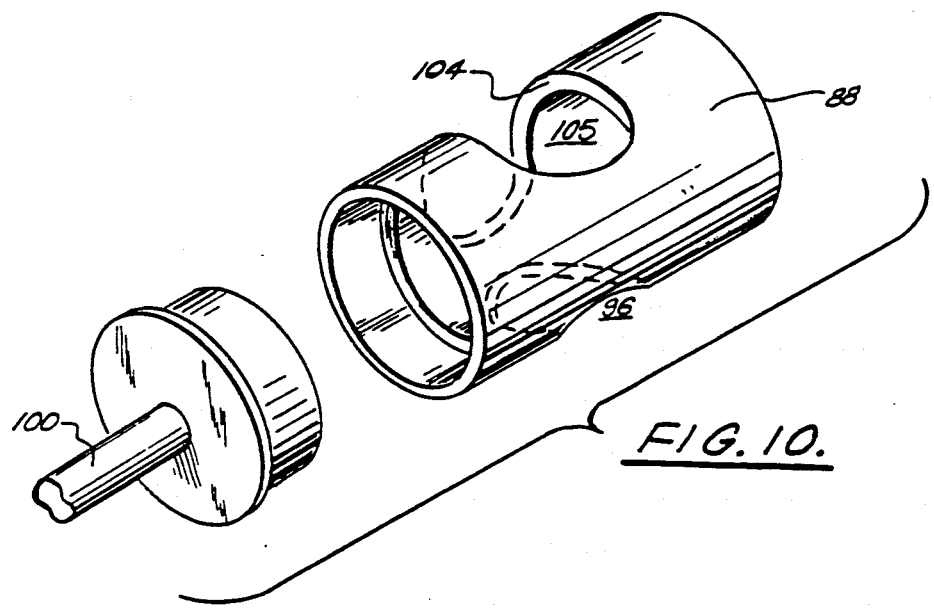
FIG. 10 is a perspective view of a portion of the unassembled cylindrical noncontaminating means of FIG. 9.

As may be seen in FIG. 9, the cylinder 88 has a cutout arcuate slot 105 formed along surface 104 which may be seen in phantom and perspective in FIG. 10. This slot 105 permits rotation of cylinder 88 without interference with tube 90. Rod 100 is sealingly engaged on bearings in casing 102 so that the high purity zone, gastight zone, or pressurized zone, as the case may be, is maintained. The integrity of the zone is maintained during collection of product in cylinder 88 by keeping a gastight valve (not shown) below tube 98 in the closed position.

The assembly shown for the cylinder 88 and rod 100 may be formed in the manner shown in FIGS. 9 and 10 or in any convenient mechanical arrangement to effect the purposes of the invention as shown in this embodiment such that solid product may be collected and then discharged from cylinder 88. Of course, the angle of repose valve 86 may be considered to include tube 90 since solid product builds up within this tube due to the angle of repose of the solid product on the surface of cylinder 88.

The embodiment of angle of repose valve 86 shown in FIGS. 9 and 10 is advantageous over angle of repose valve 68 shown in FIG. 6 in that dust and small particles of product associated with the bulk solids may escape from the valve seat support 64 due to turbulence around the bottom of tube 66. Valve 86, when in its closed position, very nearly seals arcuate surface 104 around the bottom of tube 90, thereby preventing product from gaining entry into the closed space in casing 102 which entry would permit contamination. If product is inadvertently blown out of seat 64 in FIG. 6, it can accumulate on the closed gastight valve below to cause wear when the valve is opened and permit further contamination.

Having described our invention, one skilled in the art could assertain various changes and modifications thereof which are within the scope of the disclosed apparatus and process. Thus the invention is limited only by the lawful scope of the following claims

We claim:

1. A process, in the production of silicon product in a reactor, for maintaining the purity of said silicon product and for protecting said silicon product from contamination by impurities generated by erosion of a dispensing valve through which said silicon product is discharged from said reactor, said process comprising the steps of:
   (a) fluidizing a heated bed of silicon seed particles with a gas stream comprising a silicon-containing compound in a reactor having a gas-tight dispensing valve below said reactor and an angle of repose valve comprising a non-contaminating surface between said reactor and said gas-tight dispensing valve, so as to thermally decompose said silicon-containing compound and deposit silicon on said seed particles to form silicon product;
   (b) collecting said silicon product on said non-contaminating surface in an amount such that the collected silicon product forms a pile having a sloping surface angle equal to the angle of repose of said silicon product whereby said pile of silicon product blocks the flow of solids through said angle of repose valve;
   (c) opening said gas-tight dispensing valve; and
   (d) unblocking the flow of and discharging said silicon product from said non-contaminating surface through said open dispensing valve so that said silicon product free falls through said open dispensing valve without significantly contacting said dispensing valve, thereby (1) reducing erosion of said dispensing valve and (2) protecting said silicon product from contamination by impurities generated by erosion of said dispensing valve.

2. The process of claim 1, which includes in step (d), applying a non-contaminating gas to said pile of silicon product accumulated on said non-contaminating surface, to transfer said silicon product from said non-contaminating surface, thereby unblocking the flow of said silicon product and discharging the same from said non-contaminating surface.

3. The process of claim 1, wherein in step (d) said non-contaminating surface is rotated to transfer said silicon product from said non-contaminating surface, thereby unblocking the flow of said silicon product and discharging the same from said non-contaminating surface.

4. The process of claim 1, wherein said non-contaminating surface is defined by the inner surface of a cylinder, and in step (d) said cylinder is rotated to remove said silicon product from said non-contaminating surface thereby unblocking the flow of said silicon product and discharging the same from said non-contaminating surface.

5. The process of claim 1, wherein said non-contaminating surface is within a serpentine flow path.

6. The process of claim 5, which includes in step (d) applying a non-contaminating gas to said pile of silicon product accumulated on said non-contaminating surface to transfer said silicon product from said non-contaminating surface through said serpentine flow path beneath said non-contaminating surface.

* * * * *